(12) United States Patent
Green et al.

(10) Patent No.: US 6,641,829 B1
(45) Date of Patent: Nov. 4, 2003

(54) TOPICAL APPLICATION OF SOLID ANTIMICROBIALS TO CARPET PILE FIBERS DURING CARPET MANUFACTURE

(75) Inventors: David E. Green, Simpsonville, SC (US); Leland G. Close, Spartanburg, SC (US)

(73) Assignee: Milliken & Company, Spartanburg, SC (US)

( * ) Notice: Subject to any disclaimer, the term of this patent is extended or adjusted under 35 U.S.C. 154(b) by 0 days.

(21) Appl. No.: 10/277,657

(22) Filed: Oct. 22, 2002

(51) Int. Cl.[7] .............................. A61K 9/00; A01N 25/00
(52) U.S. Cl. ........................ 424/405; 424/400; 28/100
(58) Field of Search .................... 424/400, 405, 424/443; 524/914; 28/100

(56) References Cited

U.S. PATENT DOCUMENTS 5,126,138 A * 6/1992 McGee et al. ............... 424/404
6,342,212 B1 * 1/2002 Schuette et al. ............ 424/78.1
2003/0035951 A1 * 2/2003 Magill et al. ................ 428/373

* cited by examiner

*Primary Examiner*—Thurman K. Page
*Assistant Examiner*—Simon J. Oh
(74) *Attorney, Agent, or Firm*—Terry T. Moyer; William S. Parks

(57) ABSTRACT

Carpeted floor covering articles comprising carpet pile fibers to which a topical antimicrobial application of solid particles has been applied either during or after product manufacture (such as part of a cleaning or treatment process) are provided. Such a topical treatment includes specific inorganic antimicrobial metal ion-based solid compounds, such as silver ion-exchange compounds, silver zeolites, and/or silver glasses, which may or may not be dispersed within a liquid medium for ease in handling and application. Such treatments also optionally include compositions of stain resistant agents, anti soil-redeposition compounds and liquids, surfactants, antistatic agents, and the like, to impart other characteristics to the target carpeted products. Such carpeted products thus exhibit excellent antimicrobial characteristics at both the surface of the carpet pile, as well as within the pile itself. Furthermore, it has been found that application of such solid metal-ion based antimicrobials permits the ability to increase antimicrobial activity for the target carpet product after vacuuming.

6 Claims, No Drawings

TOPICAL APPLICATION OF SOLID ANTIMICROBIALS TO CARPET PILE FIBERS DURING CARPET MANUFACTURE

FIELD OF THE INVENTION

This invention relates to carpeted floor covering articles comprising carpet pile fibers to which a topical antimicrobial application of solid particles has been applied either during or after product manufacture (such as part of a cleaning or treatment process). Such a topical treatment includes specific inorganic antimicrobial metal ion-based solid compounds, such as silver ion-exchange compounds (including silver zirconium phosphates, silver zeolites, and/ or silver glasses), which may or may not be dispersed within a liquid medium for ease in handling and application. Such treatments also optionally include compositions of stain resistant agents, anti soil-redeposition compounds and liquids, surfactants, antistatic agents, and the like, to impart other characteristics to the target carpeted products. Such carpet products thus exhibit excellent antimicrobial characteristics at both the surface of the carpet pile, as well as within the pile itself. Furthermore, it has been found that application of such solid metal-ion based antimicrobials permits the ability to increase antimicrobial activity for the target carpet product after vacuuming.

DISCUSSION OF THE PRIOR ART

All U.S. Patents listed below are herein entirely incorporated by reference.

There has been a great deal of attention in recent years given to the hazards of bacteria contamination from potential everyday exposure. Noteworthy examples of such concern include the fatal consequences of food poisoning due to certain strains of *Eschericia coli* being found within undercooked beef in fast food restaurants; Salmonella contamination causing sicknesses from undercooked and unwashed poultry food products; and illnesses and skin infections attributed to *Staphylococcus aureus, Klebsiella pneumoniae,* yeast, and other unicellular organisms. With such an increased consumer interest in this area, manufacturers have begun introducing antimicrobial agents within various household products and articles. For instance, certain brands of polypropylene cutting boards, liquid soaps, etc., all contain antimicrobial compounds. The most popular antimicrobial for such articles is triclosan. Although the incorporation of such a compound within liquid or certain polymeric media has been relatively simple, other substrates, including the surfaces of textiles and fibers, have proven less accessible. Furthermore, triclosan includes chlorine ions that, upon dissociation, may release to the substrate surface. Such ions are potentially hazardous to humans, due to skin irritation upon contact, as well as within environmental effluents, and the like. Additionally, harmful microbes have shown, on occasion, an ability to develop an immunity to the bactericidal properties of triclosan. Also, surface treatments with triclosan have proven ineffective as well since such compounds are highly water soluble and are easily removed upon exposure to sufficient amounts of moisture.

Carpets, particularly the pile portion of carpets (e.g., the portion which is designed to be in contact with pedestrians' footwear, such as tufted fibers, cut pile fibers, loop pile fibers, and the like), is highly susceptible to bacteria, fungi, and other types of microorganism contamination. With pedestrians walking on such surfaces with footwear, bare feet, and the like, not to mention the likelihood of liquid spills, crumbs, and other bacterial and fungal nutrients being relatively high, the transfer of bacteria and fungi, not to mention the facilitation of sustenance and growth of such microorganisms, are likely as well. Certain cleaning methods, such as steam cleaning, seem to increase the growth rate over time of such microorganisms as well by leaving an aqueous environment within the carpet surface portion for nutrient growth and thus subsequent microorganism sustenance and growth. Although the bacteria or fungi may be hindered by high temperature exposure during such cleaning, once the temperature level returns to normal, such microorganisms can return from dormancy. Antimicrobials have been applied to carpet backings to prevent adhesive failure and thus delamination of the pile portion from the backing itself. Furthermore, some antimicrobial application to carpet pile portions have occurred as well, including U.S. Pat. No. 5,096,747 to Scholla et al., that discloses a carpet to which a simultaneous treatment of stain resist and antibacterial compounds has been applied. However, patentees disclose anionic and/or nonionic types of antimicrobials, such as, preferably, glutaraldehyde, Microban X-580 (isopropanol, p-di-isobutylphenoxyethoxy-bromine complex, and n-octyl-bicycloheptane-di-carboxyimide, piperonylbutoxide, and pyrethrin), and phosphoric acid; there is no mention anywhere within this patent of metal-based, let alone metal-ion based inorganic antimiorobials. Such prior art antimicrobials appear to exhibit deficiencies, such as lack of long-term efficacy (and thus requirement of repeated treatments for continued high antimicrobial performance levels), and potential bacterial immunity. Also, U.S. Pat. No. 5,503,840 discloses the utilization of coated barium sulfate particles (with silver, copper, alumina, silica, and diocyl azelate) for utilization as an antimicrobial within carpet fibers and yarns, not as a topical application thereon. There thus remains a long-felt need to provide a short- and long-term effective, durable, and long-lasting topically applied antimicrobial agent for carpet pile surfaces and products. Specific metal ion-containing (such as $Ag^+$-containing, for example) inorganic microbiocides (e.g., ion-exchange compounds, such as zirconium phosphates, glasses, and/or zeolite compounds) have recently been developed and utilized as antimicrobial agents on and within a plethora of different substrates and surfaces. These types of antimicrobials are highly desirable because of their ability to provide efficacy in antimicrobial activity, without fear of bacterial or fungal immunity thereto, not to mention the lack of highly oxidative moieties and pendant groups (such as chlorine-based compounds) that can provide harmful irritation and potentially unpleasant smells, as well as the ease in handling of such solid particulates in general, create a desire to employ such compounds within many different media. In particular, such microbiocides have been adapted for incorporation within plastic compositions and fibers in order to provide household and consumer products which inherently exhibit antimicrobial characteristics. Although such silver-based agents provide excellent, durable, antimicrobial properties, to date no teachings exist which teach or fairly suggest the presence of such inorganic compounds as durable topical applications on carpet pile fibers. This is not surprising considering the difficulties in providing a durable topical application of solid particles on any surface, let alone specific carpet pile surfaces and fibers. The propensity of such solid particulates to gravitate to the bottom of such carpet pile structures, and thus seemingly fail to provide effective antimicrobial performance throughout such fibers (i.e., at the top portion, at the middle portion, and at the bottom portion, simulatneously) has militated against attempting such a treatment. This nonuniformity in protection thus requires amelioration prior to effective utilization of such highly desired antimicrobial agents. To date, such an obstacle has not been overcome to permit widespread utilization of such antimicrobials within carpet pile structures.

DESCRIPTION OF THE INVENTION

It is thus an object of the invention to provide a simple manner of effectively treating a carpet pile portion of a floor covering article with a durable antimicrobial metal-ion containing antimicrobial treatment during the initial manufacture of the article itself. A further object of the invention is to provide a simple manner of effectively treating a carpet pile portion of a floor covering article with a durable antimicrobial metal-ion containing antimicrobial treatment in a cleaning or post-cleaning procedure. Another object of the invention is to provide a simple manner of effectively treating a carpet pile portion of a floor covering article with a durable antimicrobial metal-ion containing antimicrobial treatment that also imparts antiftingal and odor-reduction characteristics thereto.

Accordingly, this invention encompasses a floor covering article including a carpeted component wherein at least a portion of said carpeted component is topically treated with a solid antimicrobial and wherein said carpeted component of said floor covering article exhibits a log kill rate for *Klebsiella pieumoniae* of at least 1.0, preferably above 1.5, more preferably above 2.0 as tested in accordance with AATCC Test Method 100–1999 for 24 hour exposure, after at least 2 standard carpet shampoo treatments in accordance with AATCC Test Method 138. Such an invention also encompasses the different methods of topically treating such an inventive carpeted floor covering article. The shampoo durability test noted above is standard and, as will be well appreciated by one of ordinary skill in this art, is not intended to be a required or limitation within this invention. Such a test method merely provides a standard which, upon 2 shampoos in accordance with such, the inventive treated carpeted floor covering article will not lose an excessive level of its antimicrobial efficacy.

The effective amount of solid antimicrobial retained may be measured in any standard manner, such as, for example, inductively coupled plasma (ICP), X-ray fluorescence (XRF), or atomic absorption (AA) spectroscopic analysis. However, again, in the alternative, the durability of such topically applied carpet treatments are preferably determined (i.e., the retention of treatment on the carpet pile surface) in relation to antimicrobial performance. Thus, with an antimicrobially effective treatment, the exhibition of log kill rate for *Klebsiella pneumoniae* after 24 hours exposure in accordance with AATCC Test Method 100–1999 of at least 1.0, and higher, as noted above, after 2 standard shampoos in accordance with AATCC Test Method 138 is indication of the proper and necessary amount of solid antimicrobial retained and/or still antenicrobially effective for minimum acceptable performance. Preferably, these log kill rates are above 1.2, more preferably 1.5, and most preferably at least 2.0. Again, such log kill rates after the minimum number of shampoos symbolizes the desired durability level noted above.

Nowhere within the prior art has such a specific treated carpeted floor covering or method of making thereof been disclosed, utilized, or fairly suggested. The closest art, Scholla et al., noted above, names certain liquid antimicrobials as potential co-additives to carpet pile structures simultaneously with certain stain-resist finishes. No solid antimicrobial, let alone metal-ion containing solid antimicrobial, let alone silver-ion containing antimicrobial compounds are taught nor fairly suggested. All other prior art discusses the extrusion of solid antimicrobials within fibers, which may include carpet fibers, to impart antimicrobial characteristics to the target floor covering article. However, nowhere has such a durable topical treatment as described broadly above been mentioned or alluded to.

Any standard carpet yam or fiber may be utilized as the substrate for topical treatment thereof within this application. Thus, natural (cotton, wool, and the like) or synthetic fibers (polyesters, polyamides, polyolefins, and the like) may constitute the target substrate, either by itself or in any combinations or mixtures of synthetics, naturals, or blends or both types. As for the synthetic types, for instance, and without intending any limitations therein, polyolefins, such as polyethylene, polypropylene, and polybutylene, halogenated polymers, such as polyvinyl chloride, polyesters, such as polyethylene terephthalate, polyester/polyethers, polyamides, such as nylon 6 and nylon 6,6, polyurethanes, as well as homopolymers, copolymers, or terpolymers in any combination of such monomers, and the like, may be utilized within this invention. Nylon-6, nylon-6,6, polypropylene, and polyethylene terephthalate (a polyester) are particularly preferred. In general, the carpet pile portion of the target floor covering article should include at least some synthetic fibers as it appears that the solid metal-ion based antimicrobial compounds are more effective when applied to such fiber materials. Without intending to be bound to any specific scientific theory, it is believed that such solid antimicrobials become more easily attracted to and/or embedded within the synthetic types of fibers (polyamides and polyesters, for example) than for the natural fibers (wool, for example). Additionally, the target fibers may include additives coextruded therein, may be precoated with any number of different materials, including those listed in greater detail below, and/or may be dyed or colored to provide other aesthetic features for the end user with any type of colorant, such as, for example, poly(oxyalkylenated) colorants, as well as pigments, dyes, tints, and the like. Other additives may also be present on and/or within the target fiber or yam, including antistatic agents, brightening compounds, nucleating agents, antioxidants, UV stabilizers, fillers, permanent press finishes, softeners, lubricants, curing accelerators, and the like. Particularly desired as optional and supplemental finishes to the inventive fabrics are soil release or anti-redeposition agents which improve the hydrophobicity and cleanability of the carpet pile yarns and fibers (such as SCOTCHGUARD, for example). Additionally, other potential additives and/or finishes may include water repellent fluorocarbons and their derivatives, silicones, waxes, and other similar water-proofing materials.

The particular treatment preferably comprises at least one type of solid metal-ion containing particles, or mixtures thereof. The term metal is intended to include any such historically understood member of the periodic chart (including transition metals, such as, without limitation, silver, zinc, copper, nickel, iron, magnesium, manganese, vanadium, gold, cobalt, platinum, and the like, as well as other types including, without limitation, aluminum, tin, calcium, magnesium, antimony, bismuth, and the like). More preferably, the metals utilized within this invention are generally those known as the transition metals. Of the transition metals, the more preferred metals are silver, zinc, gold, copper, nickel, manganese, and iron. Most preferred are silver and zinc. Such metals provide the best overall desired characteristics, such as, preferably, antimicrobial, antifungal, and/or odor reducing characteristics, certain colorations, good lightfastness, and, most importantly, shampoo durability on the target carpet pile substrate.

The preferred metal-ion containing compound for this invention is an antimicrobial silver zirconium phosphate available from Milliken & Company, under the tradename ALPHASAN®, although any silver-containing antimicrobial compound, including, for instance, and as merely some examples, a silver-substituted zeolite available from Sinanen under the tradename ZEOMIC®, or a silver-substituted glass available from Ishizuka Glass under the tradename IONPURES®, may be utilized either in addition to or as a substitute for the preferred species. Also preferred as such a compound is zinc oxide, zinc ricinoleate, zinc chloride, and zinc sulfate. Other metals, as noted above, may also be utilized; however, from a performance standpoint, silver and zinc, are preferred; however, silver ion-containing types are most preferred. Generally, such a metal compound is added in an amount of from about 0.01 to 60% by total weight of the particular treatment composition; more preferably from about 0.05 to about 50%; and most preferably from about 0.1 to about 50% (depending on the target use; with liquids, the amount is very low due to ability to deliver sufficient amounts of antimicrobial during liquid treatments, whereas the amounts within solid mixes are rather large due to lower amounts of solid being contacted with target pile surfaces; thus, with solid topical applications, relatively high amounts of antimicrobial within the initial mix delivers sufficient antmicrobial levels during use). Therefore, the metal-ion containing compound is added, as an active, to the target substrate via delivery from either a liquid (shampoo, for example) or solid medium, in amounts of between 100 and 15000 ppm on the weight of the face fiber (owff), more preferably from between 150 to about 14000 ppm, still more preferably from 175 to 13000 ppm, and most preferably between 200 and 12000 ppm (which translates into roughly 0.02 to 1.2% by weight owff). Such proportions provide the best antimicrobial and/or odor-reducing performance in relation to wash durability, electrical non-conductivity, and overall cost, not to mention the best potential for sufficient amounts to remain embedded within the target fibers after further and/or future vacuum or other cleaning procedures are undertaken. The treatment itself, including any necessary binders, adherents, thickeners, and the like, is added to the substrate in an amount of a) about 0.02 to about 8.0 ounces per square yard, or b) from about 0.1 to about 20% owff Other possible compounds, again without limitation, are silver-based materials such as AMP® T558 and MICROFREE®, both available from DuPont, as well as JMAC®, available from Johnson Mathey.

The treatment compositions and formulations thus include such metal-ion containing compounds as antimicrobial, anti-fouling, anti-fungal, and anti-odor components. Such compounds are thus delivered to the target pile surfaces simultaneously with different pile surface additives and treatment agents, including, without limitation, bleach resistance agents, colorsafe agents, water- and/or color-repellent agents, stain blockers, stain resists, and the like, as well as binding agents to facilitate adhesion of the solid antimicrobials to the target pile fibers. Preferably, such antimicrobial, etc., compounds are admixed or dispersed within bleach resistance formulations or water and/or dye-repellent formulations. Such formulations comprise, for bleach resistant types, any bleach resistant compounds for pile surfaces, such as, for example, methyl paraben, foaming agents, such as any of various anionic or nonionic surfactants, including, without limitation, fatty aryl-sulfonates, -phosphates (preferably dodecylbenzenesulfonic acid), and the like, and/or ethoxylated fatty alcohols (preferably Syn Lube® 728 from Milliken & Company), and a stain blocking or binding agent, such as an acrylate (or like type of compound)(such as Acrysol® ASE-75 from Rohm and Haas which can fulfill both requirements). Further additives may include further foaming agents (such as coconut oil), antistatic agents, and the like. Such bleach resistant formulations are preferably aqueous in nature (although short-chain alcohols, such as methanol, ethanol, isopropanol, and the like, may also be utilized as the solvent therein) may be in the form of a shampoo, coating, spray, atomized dispersion, and the like, with a shampoo the preferred delivery method.

Water- and/or dye-repellent formulations preferably comprise a fluorinated polymer for ease in adhering to the pile fibers with simultaneous excellent repellency properties introduced thereto. Such a fluoropolymer may be any well known type, including, without limitation, Zonyl® types from DuPont, Repeari® from Mitsubishi, Foraperle® 501 from Elf Atochem, and any number of fluorinated polymers available from 3M. Such formulations are generally aqueous in nature as well and applied as a spray, shampoo, or coating. A shampoo is again preferred.

The term floor covering, as noted above, is intended to cover any standard articles which comprise face fibers and which are utilized to cover surfaces on which people are prone to walk. Thus, carpets (broadloom, tile, or otherwise) and floor mats (outdoor, indoor, and the like) are the primary articles concerned within this invention. The term face fiber portion encompasses any standard fibers and composites thereof, which are utilized within floor coverings. As mere examples, nylon, polyethylene, polypropylene, cotton, polyvinylacetate, and the like, fibers may be tufted through a fabric (such as a woven, non-woven, or knit fabric of any fiber type, such as those listed previously), which happens to be what is intended to be encompassed by the term primary backing portion. Also, the face fiber portion may be monofilament, core-sheath fiber, and the like, or may be present as loop pile, cut pile, or any other type of carpet face.

Initially, prior to integration with any other components, the face fiber portion is sewn, tufted, needled, and the like, through the primary backing fabric to form a composite which can then be simply adhered to a further portion. Alternatively, the primary backing fabric may be contacted with the secondary backing fabric and the face fiber portion may then be created by the needling, etc., through the primary backing fabric. Basically, any number of alternatives are available for production of the inventive floor covering product. Examples of carpet and carpet tile production are disclosed within U.S. Pat. No. 5,929,145 to Higgins et al., U.S. Pat. No. 5,948,500 to Higgins et al., U.S. Pat. No. 5,545,276 to Higgins et al., and U.S. Pat. No. 5,540,968 to Higgins et al. Examples of floor mat production are present within U.S. Pat. No. 5,902,662 to Kerr, U.S. Pat. No. 5,928,446 to Kerr et al., and U.S. Pat. No. 5,305,565 to Nagahama et al. Preferably, a latex is utilized to adhere the face fiber portion to a secondary backing to form a stabilized composite. The latex may include an antimicrobial if desired.

The term secondary backing portion is intended to be rather broad since the important issue with regard to such a component is the contact with the latex between that layer and the primary backing fabric. Such a secondary layer then may be of any standard carpet or floor mat backing, or intermediate layer. Thus, if it is a carpet, the secondary backing may be a polyolefin fabric, or a polyurethane foam (for cushioning purposes) or simply a fabric layer to which a polyurethane foam is attached. If it is a floor mat, the secondary backing may be a sheet of solid or foamed rubber most likely, although, again, such a backing may be an intermediate layer of fabric, rubber, and the like, between the primary backing fabric and an outer layer.

The particular solid metal-ion-based antimicrobial agent should exhibit an acceptable log kill rate after 24 hours in accordance with the AATCC Test Method 100–1999. Such an acceptable level log kill rate is tested for *Staphlylococcus aureus* of at least 0.1 increase over baseline. Alternatively, an acceptable level will exist if the log kill rate is greater than the log kill rate for non-treated (i.e., no solid inorganic antimicrobial added) pile fibers (such as about 0.5 log kill rate increase over control, antimicrobial-free fibers). Preferably this log kill rate baseline increase is at least 0.3 for *S. aureus*; more preferably 0.5; and most preferably 1.0. Of course, the high end of such log kill rates are much higher than the baseline, on the magnitude of 5.0 (99.999% kill rate). Any rate in between is thus, of course, acceptable as well. However, log kill rates which are negative in number are also acceptable for this invention as long as such measurements are better than that recorded for correlated non-treated fibers. In such an instance, the antimicrobial material present within the target carpet pile fibers at least exhibits a hindrance to microbe growth.

The preferred embodiments of these alternatives fiber treatments are discussed in greater detail below.

DESCRIPTION OF THE PREFERRED EMBODIMENTS

Examples of particularly preferred treatments within the scope of the present invention are set forth below.

Antimicrobial Floor Covering Pile Surfaces Production

Typical cushioned carpet tile articles were produced in accordance with the general manufacturing processes of U.S. Pat. Nos. 5,540,968 and 5,545,276. It should be understood that any carpeted floor covering article can be produced in accordance with the broad scope of the instant invention and these carpet tile articles are merely preferred, non-limiting examples of end-use articles incorporating the inventive antimicrobial treatments. Such manufacturing procedures further include application of various potential additives, such as stain blocks, bleach protectants, and the like. Such process steps were implemented in selected variations of the inventive method of antimicrobial topical application as noted below. Preferably, such applications were achieved utilizing a foam treatment formulation including an acrylate stain blocker or bleach protectant (or both; again, as noted below), followed by a 1–2 minute steam treatment to set the additives onto the pile surface. The carpet tiles (which included carpet pile comprised of nylon-6,6 fibers for one example and polyethylene terephthalate fibers for another) were then quickly washed and vacuumed to remove excess additives. Subsequently, a fluorocarbon treatment (as noted below) was effectuated to provide water-, dye-, and/or liquid-repellency to the carpet tile article. In another potentially preferred variation of the inventive method, the antimicrobial was applied simultaneously with the fluorocarbon. After fluorocarbon application, the target carpet tile was then dried and stored for shipping to customers.

The preferred antimicrobial-containing treatment formulations were compounded in accordance with the Table below with all of the components admixed together. The manufacturing during which topical treatment was undertaken with such specific formulations are noted below in the Table as well.

Antimicrobial-containing Treatment Formulations

EXAMPLE 1

Acrylic Matrix

| Component | Amount added (% by weight) |
|---|---|
| Methyl Paraben | 30 |
| Acrysol ® ASE-75 | 8 |
| Dodecylbenzenesulfonic Acid | 4 |
| Ammonia | 1 |
| Syn Lube ® 728 plus Coconut Oil | 0.5 |
| Antimicrobial | (as listed below) |
| Water | Balance |

EXAMPLE 2

Flourocarbon Formulation

| Component | Amount added (% by weight) |
|---|---|
| Foraperle ® 501 | 2 |
| Antimicrobial | (as listed below) |
| Water | Balance |

The carpeted pile surfaces of the floor coverings made during the above non-limiting manufacturing process and treated as noted above with the specific formulations during certain process steps were then tested for antimicrobial efficacy after production as well as after 2 standard carpet shampooings (without adding any further antimicrobial additives thereto). The amount of antimicrobial applied to the target carpet tile pile portion was adjusted to uniformly equal different levels, from 200 ppm on the weight of the face fiber (owff) up to 3000 ppm owff (to test the difference between efficacy at such disparate antimicrobial levels). The log kill results were as follows for *K. pneumoniae* after 24 hours of exposure, initially and after 2 subsequent shampoo treatments in accordance with AATCC Test Method 138:

EXPERIMENTAL DATA TABLE 1
Log Kill Rates for *K. pneumoniae*
No Subsequent Fluorocarbon Treatment Added

| Ex. # (above) | Antimicrobial Type (ppm owff) | Initial or Shampooed | Log Kill Rate |
|---|---|---|---|
| 1 | ALPHASAN ® RC 5000 (200) | Initial | 1.57 |
| 1 | ALPHASAN ® RC 5000 (200) | Shampooed | 1.65 |
| 1 | ALPHASAN ® RC 5000 (1200) | Initial | 3.44 |
| 1 | ALPHASAN ® RC 5000 (1200) | Shampooed | 2.71 |
| 1 | ALPHASAN ® RC 5000 (2000) | Initial | 3.90 |
| 1 | ALPHASAN ® RC 5000 (2000) | Shampooed | 3.98 |
| 1 | ALPHASAN ® RC 5000 (3000) | Initial | 3.12 |
| 1 | ALPHASAN ® RC 5000 (3000) | Shampooed | 3.49 |
| 1 | JMAC (1200) | Initial | 3.12 |
| 1 | ZEOMIC ® | Initial | 3.24 |
| (Comparative Examples) | | | |
| 1 | None | Initial | 0.02 |
| 1 | None | Shampooed | 0.06 |

EXPERIMENTAL DATA TABLE 2
Log Kill Rates for *K. pneumoniae*
Subsequent Fluorocarbon (without Antimicrobial) Added

| Ex. # (above) | Antimicrobial Type (ppm owff) | Initial or Shampooed | Log Kill Rate |
|---|---|---|---|
| 1 | ALPHASAN ® RC 5000 (200) | Initial | 0.82 |
| 1 | ALPHASAN ® RC 5000 (200) | Shampooed | 1.09 |
| 1 | ALPHASAN ® RC 5000 (1200) | Initial | 3.82 |
| 1 | ALPHASAN ® RC 5000 (1200) | Shampooed | 3.47 |
| 1 | ALPHASAN ® RC 5000 (2000) | Initial | 2.51 |
| 1 | ALPHASAN ® RC 5000 (2000) | Shampooed | 2.98 |
| 1 | ALPHASAN ® RC 5000 (3000) | Initial | 3.11 |
| 1 | ALPHASAN ® RC 5000 (3000) | Shampooed | 2.95 |
| (Comparative Examples) | | | |
| 1 | None | Initial | −0.45 |
| 1 | None | Shampooed | 0.07 |

EXPERIMENTAL DATA TABLE 3
Log Kill Rates for *K. pneumoniae*
Subsequent Fluorocarbon (with Antimicrobial) Added;
No Acrylate Added

| Ex. # (above) | Antimicrobial Type (ppm owff) | Initial or Shampooed | Log Kill Rate |
|---|---|---|---|
| 2 | ALPHASAN ® RC 5000 (1100) | Initial | 3.82 |
| 2 | ALPHASAN ® RC 5000 (1100) | Shampooed | 2.63 |
| 2 | ALPHASAN ® RC 5000 (2000) | Initial | 3.98 |
| 2 | ALPHASAN ® RC 5000 (2000) | Shampooed | 3.34 |
| 2 | ALPHASAN ® RC 5000 (2600) | Initial | 3.69 |
| 2 | ALPHASAN ® RC 5000 (2600) | Shampooed | 3.26 |
| (Comparative Examples) | | | |
| 2 | None | Initial | 0.41 |
| 2 | None | Shampooed | 0.10 |

Thus, the inventive manufactured carpeted floor coverings exhibited excellent durable antimicrobial properties.

There are, of course, many alternative embodiments and modifications of the present invention which are intended to be included within the spirit and scope of the following claims.

What we claim is:

1. A method of topically treating a carpeted floor covering article during the manufactures of said article, said method comprising the steps of (a) providing a carpeted floor covering article, wherein said article comprises a pile component and a primary backing component;

(b) contacting at least a portion of said pile component with a formulation comprising at least one solid metal-ion containing antimicrobial and at least one coadditive selected from the group consisting of at least one fluorochemical, at least one binding agent, and any mixture thereof, wherein said antimicrobial is present at both the surface of said pile and within said pile;

wherein said carpeted component of said floor covering article exhibits a log kill rate for *Klebsiella pneumoniae* of at least 1.0, as tested in accordance with AATCC Test Method 100–1999 for 24 hour exposure, after at least 2 standard carpet shampoo treatments in accordance with AATCC Test Method 138.

2. The floor covering article of claim 1 wherein said metal-ion containing antimicrobial agent is a silver-ion based compound.

3. The floor covering article of claim 2 wherein said silver-ion based compound is a silver ion-exchange compound.

4. A method of topically treating a carpeted floor covering article during the manufacture of said article, said method comprising the steps of (a) providing a carpeted floor covering article, wherein said article comprises a pile component and a primary backing component;

(b) contacting at least a portion of said pile component with a formulation comprising at least one solid metal-ion containing antimicrobial and at least one coadditive selected from the group consisting of at least one fluorochemical, at least one binding agent, and any mixture thereof, wherein said antimicrobial is present at both the surface of said pile and within said pile;

wherein said carpeted component of said floor covering article exhibits a log kill rate for *Klebsiella pneumoniae* of at least 1.0, as tested in accordance with AATCC Test Method 100–1999 for 24 hour exposure.

5. The method of claim 4 wherein said silver-ion based compound is a silver ion-exchange compound.

6. The floor covering article of claim 5 wherein said silver-ion based compound is a silver ion-exchange compound.

* * * * *

UNITED STATES PATENT AND TRADEMARK OFFICE
CERTIFICATE OF CORRECTION

PATENT NO.        : 6,641,829 B1
APPLICATION NO. : 10/277957
DATED              : November 4, 2003
INVENTOR(S)       : David E. Green and Leland G. Close It is certified that error appears in the above-identified patent and that said Letters Patent is hereby corrected as shown below:

In Claim 1, line 3, delete the word "manufactures" and insert the word --manufacture--.

In Claim 1, line 17, delete the word "carpeted" and insert the word --pile--.

In Claim 2, line 24, delete the words "floor covering article" and insert the word --method--.

In Claim 3, line 27, delete the words "floor covering article" and insert the word --method--.

In Claim 4 (b), line 45, delete the word "carpeted" and insert the word --pile--.

In Claim 6, line 51, delete the words "floor covering article" and insert the word --method--.

Signed and Sealed this

Twenty-second Day of August, 2006

JON W. DUDAS
*Director of the United States Patent and Trademark Office*